United States Patent [19]

Shah

[11] 4,328,353

[45] May 4, 1982

[54] PROCESS FOR THE MANUFACTURE OF ORGANOHALOSILANES

[75] Inventor: Bakulesh N. Shah, Clifton Park, N.Y.

[73] Assignee: General Electric Company, Waterford, N.Y.

[21] Appl. No.: 248,779

[22] Filed: Mar. 30, 1981

[51] Int. Cl.$^3$ .......................... C07F 7/08; C07F 7/12; C07F 7/16

[52] U.S. Cl. .................. 556/472; 556/465; 556/466

[58] Field of Search ........................................ 556/472

[56] References Cited

U.S. PATENT DOCUMENTS 2,803,521  8/1957  Nitzsche et al. ............... 556/472 X 3,655,709  4/1972  Fries et al. ........................ 556/472

FOREIGN PATENT DOCUMENTS 731174  3/1966  Canada ............................. 556/472

Primary Examiner—Paul F. Shaver
Attorney, Agent, or Firm—Michael J. Doyle

[57] ABSTRACT

There is provided an improved process for removing residual silicon and copper powder from the gaseous organohalosilane products of a direct process reactor which utilizes sintered metal filtering elements to filter out the said powder from gaseous organoalosilanes which have been processed in primary and secondary cyclones.

11 Claims, 2 Drawing Figures

PROCESS FOR THE MANUFACTURE OF ORGANOHALOSILANES

FIELD OF THE INVENTION

The present invention relates to an improved process for the manufacture of organohalosilanes in a fluidized bed reaction wherein residual silicon and copper powder impurities are removed from gaseous halosilanes by utilization of an array of sintered metal filters and an alkylhalide blowback system.

BACKGROUND OF THE INVENTION

The present commercial method for manufacturing organohalosilanes is well known and is described in U.S. Pat. No. 2,380,995-Rochow. Rochow discloses the direct reaction of an organohalide such as methylchloride with silicon particles in order to produce organochlorosilane. Intermixed with such particles of silicon are particles of copper, thereby forming a reactive mass. In commercial practice this reaction is generally carried out in one of three types of equipment: the stirred bed type of reactor as described in Sellers U.S. Pat. No. 2,449,821, the fluidized bed reactor described in Reed, et al. U.S. Pat. No. 2,389,931, or the rotary kiln.

Organotrichlorosilanes and diorganodichlorosilanes are the two basic products of the above described "direct process" reaction. Such compounds are utilized in the production of organopolysiloxane resins as described in U.S. Pat. Nos. 2,258,218 through 2,258,222. Other products include organopolysiloxane fluids as described in U.S. Pat. No. 2,469,888 and U.S. Pat. No. 2,469,890 as well as the organopolysiloxane elastomers described in U.S. Pat. No. 2,448,756. These patents are generally considered to be the pioneers in the polysiloxane area. Since that time the silicone industry has experienced substantial innovation in this field and a substantial patent literature has evolved relating to the different types of compositions that can be produced from basic organochlorosilanes. It is preferable to produce the diorganodichlorosilanes in a high production manner since they can be utilized most widely, particularly in producing the linear polysiloxane fluids and polymers used in the production of heat cured rubber elastomers and room temperature vulcanizable silicone rubber compositions of various types.

There have been numerous improvements to the direct process for producing alkylhalosilanes as described above. Of particular interest is a method disclosed in copending patent applications of Shah and Ritzer Ser. No. 193,761 filed Oct. 3, 1980, and Ser. No. 209,635 filed Nov. 24, 1980, which are hereby incorporated by reference. These patent applications describe a method for classifying by particle size the residual silicon powder contact mass from the fluidized reactor bed thereby enabling the recycling of substantial amounts of relatively pure silicon powder at a great cost savings.

Although the present invention can be useful in the manufacture of many organohalosilanes, the present disclosure is particularly related to a process for the manufacture of methylchlorosilanes by reacting metallurgical grade silicon with methylchloride at 250° to 350° C. in the presence of copper, followed by condensation and separation of methylchlorosilanes from the crude reaction product mixture.

The gaseous mixture of methylchlorosilanes and unreacted methylchloride will entrain particles of residual contact mass powder from the fluid bed reactor. The gaseous mixture passes through a series of cyclones where most of the powder is separated from the gaseous crude. Such cyclones are never one hundred percent efficient and there is always some residual powder left in the gaseous crude after it leaves the last cyclone. This powder must be removed from the gaseous crude before condensation. If condensation is carried out before removing this powder, the inside surfaces of the condensers will become encrusted with the silicon and copper powder and will become clogged as the condenser passages become obstructed. Furthermore, the downstream separation unit will also become encrusted and plugged in a similar manner. Consequently, after a short running time, the system has to be stopped, opened up and cleaned out. One way of removing the fine powder is to use a scrubber-revaporizer system. With such a system, the powder-laden gas crude flows countercurrent to a stream of liquid chlorosilanes in a scrubbing tower with sieve plates. The liquid flows down from the top and entrains the powder in slurry form which flows out of the scrubber into a vessel called the revaporizer. The scrubbed gaseous crude then flows out of the scrubber from the top and is condensed. The relatively dilute slurry may be concentrated in the revaporizer by heating and constantly agitating the slurry. This is a necessary procedure because of the valuable chlorosilanes contained in the slurry. The vapors formed in the revaporizer are passed back into the scrubber. The concentrated slurry in the revaporizer may be disposed by incineration. This method of removing powder from gaseous crude has a particular disadvantage in that it leads to the loss of fine silicon and copper powder from the slurry as well as the loss of some chlorosilanes. Additionally, there is significant energy consumption in the revaporizer and the incinerator. It was therefore felt that considerable savings could be accomplished if some or all of these disadvantages could be avoided. Furthermore, the use of a revaporizer is a relatively difficult operation because of the mixing requirement and the need to transfer the thick slurry and the agitator seals on such equipment require periodic and costly maintenance. Furthermore, not only is the transport of the thick slurry often a difficult operation, at times the slurry will set like hard cement requiring costly shutdown in order to dig out the hard crust.

It is therefore an object of the present invention to provide a process for removing the residual powder from the gaseous crude of organohalosilanes from a direct process fluidized reactor bed.

It is a further object to provide a process for removing residual silicon and copper powder in a less costly and burdensome manner than heretofore available.

It is another object to eliminate the necessity of a scrubber-vaporizer in a direct process organohalosilane system.

It is another object of the present invention to provide relatively pure gaseous organohalosilane mixtures which do not contain residual reactor mass fines.

These and other objects will become apparent to those skilled in the art upon consideration of the following specification, claims and accompanying drawings.

SUMMARY OF THE INVENTION

The present invention provides a process for purifying the gaseous organohalosilane products of a direct process reactor such as a methylchlorosilane reactor comprising the steps of (a) directing a stream of powder-laden gaseous organohalosilane products to a filter vessel containing an array comprised of at least one or a plurality of sintered metal filters. It is contemplated by the present invention that the gaseous organohalosilane products may particularly be any of the many methylchlorosilane products used in the silicone industry. Such gaseous organohalosilane products are powder-laden with silicon and copper powders which are entrained by the gas as it escapes from the direct process fluid bed reactor. It is these silicon and copper powder particles which are intended to be recovered and recycled by the process of the present invention. The filter vessel will contain one or more of such sintered metal filter elements. The residual powders are separated from such gaseous organohalosilanes as the gas passes through the sintered metal filters thereby depositing a layer of the powder on the outer surface of the filter. The filtering process will continue until the relative pressure drop across the filter element becomes large. At this time, the powder is recovered from the filter element by first halting the flow of the powder-laden gaseous organohalosilane products through the filter thereupon a stream of hot blowback gas is directed through the filter in a direction opposite to the original flow of the gaseous organohalosilane products. By pulsing the blowback process for periods of 0.5 to 5 seconds, it is possible to maintain a relatively constant average pressure drop across the filtering elements for any given reaction period, as long as the pores do not continually keep plugging. The blowback gas blows the residual powder from the filtering elements and this powder material can be recovered from the bottom of the filter vessel and recycled or discarded.

It is to be noted nearly any blowback gas can be utilized but ordinarily for such a process, methylchloride gas is preferred. Methylchloride offers several advantages over other blowback gases. First, methylchloride is ordinarily readily available in large quantities for use in the direct process reactions described above. Furthermore, methylchloride gas can be utilized as the blowback agent without fear of contaminating the organohalosilane process stream with impurities from other blowback agents. And furthermore, the methylchloride gas can be recovered and recycled to the direct process reactor if desired. Of course other inert gases could be utilized as well as the gaseous organohalosilane products made in the present direct process.

DESCRIPTION OF THE PREFERRED EMBODIMENT

The process of the present invention is particularly well suited for use with the manufacture of methylchlorosilanes wherein it is possible to remove the residual powder from gaseous chlorosilanes without experiencing the aforementioned problems. This object is achieved by incorporating sintered metal filters in a vessel in the line coming from the last cyclone. Such sintered metal filters are effective for screening out the powder while allowing clean gaseous crude to flow directly to the condensers. Periodically it is necessary that the powder be blown off the filtered surfaces by passing any hot gas in the reverse direction. Ordinarily hot methylchloride gas is quite suitable for this.

Figure 1:
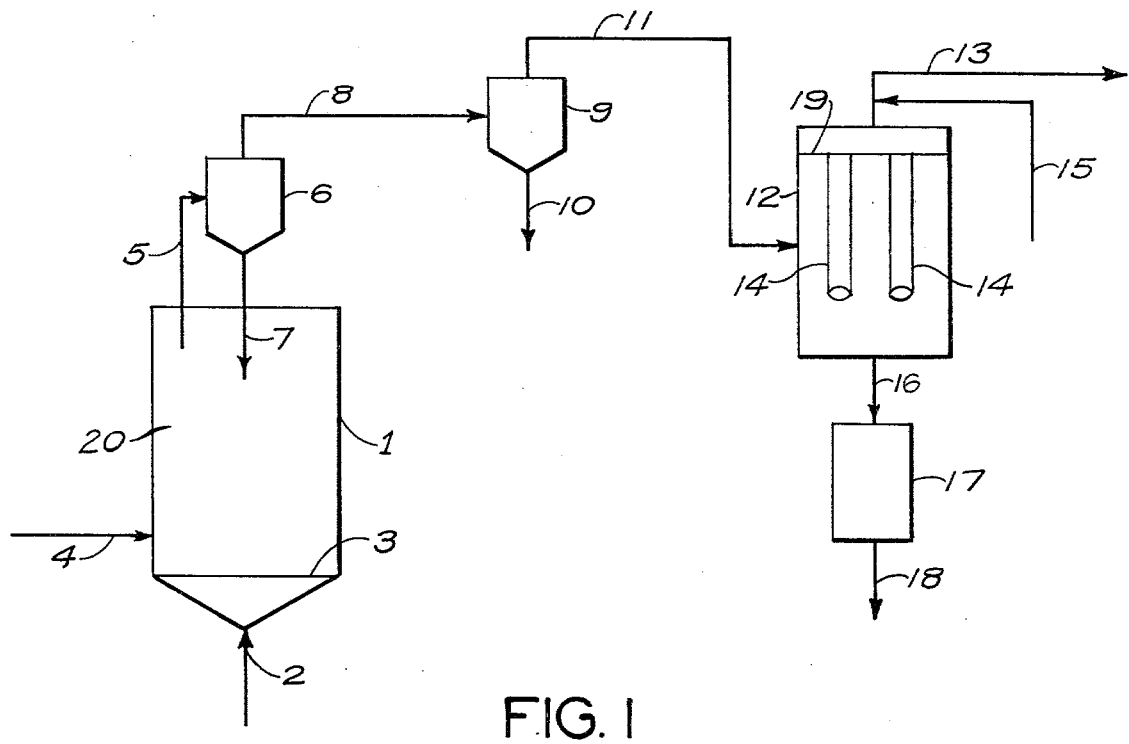
FIG. 1 is a process flow diagram depicting the recovery of powder-laden gaseous crude from an organohalosilane reactor system and the purification thereof by an array of sintered metal filters utilized in the process of the present invention.

The process of the present invention will be better understood with reference to FIG. 1. Gaseous methylchloride is blown into the bottom of fluid bed reactor 1 through inlet line 2. This gas flows upward through sieve plate 3 and through a fluidized bed of silicon and copper contained in the reactor. The copper and silicon powder are introduced continuously into the reactor through inlet line 4. The methylchloride reacts with the silicon in the fluidized bed to produce methylchlorosilanes. The particular silanes of most interest are dimethyldichlorosilane, methyltrichlorosilane, trimethylchlorosilane and a series of other gaseous reaction products. Of course, it is to be emphasized that such an alkylhalosilane reaction system need not be limited to the methylchlorosilanes series of products. The direct process reaction is carried out at a temperature of approximately 250°–350° C. and preferably in the range of approximately 280°–300° C. The product gases which carry some residual powder from the fluid bed reactor leave the reactor through line 5 and enter cyclone 6 wherein a large amount of the residual powder may be recovered. As mentioned earlier, not all of the residual powder is so recovered since cyclone efficiency is not one hundred percent. The separated powder from cyclone 6 drops back into reactor 1 through line 7 and is reutilized therein. The product gases containing remaining residual powder leaves cyclone 6 through line 8 and enters cyclone 9 where additional powder is removed from the gases. This powder drops out of the cyclone through line 10 where it can be collected and reutilized or discarded. Next the product gases which still contain some residual powder leave cyclone 9 through line 11 and are directed to the sintered metal array utilized in the process of the present invention. Additional cyclones could be utilized for further removal of powder from the product gases but these would not be economical because the efficiency of a cyclone drops rapidly when the size of the powder to be removed is in the range of just a few mirons.

In accordance with the process of the present invention the powder-laden product gas is then directed through line 11 to vessel 12 wherein one or more sintered metal filter elements 14 are arranged in an array to filter out the powder. The number of filter elements 14 required in this process depends on the process parameters at any particular time. Those skilled in the art will be able to utilize a proper number of sintered metal filters for effectively removing the powder contained in the gaseous product without undue experimentation. The important design criterion for selecting the proper number of filters is the filter surface velocity of the gas which is to be filtered. The velocity should be such so as to prevent continuous penetration of powder particles into the filter medium. The velocity should not normally exceed 10 ft/min at the filter surface and preferably will be approximately 3 to 5 ft/min.

As an example, if the flow rate of the powder-laden gas is 1000 cubic ft/min at a selected process temperature and pressure, then for a chosen filter surface velocity of 4 ft/min the filter area requirement is 1000÷4=250 square feet. Then, given filters of fixed length and diameter for each element, the surface area for each element can be determined and the total number of elements in the filter array can be calculated. The residual powder is deposited on the outside of filter elements 14 while the gaseous crude product passes through the filter elements. The powder-free crude gas leaves filter vessel 12 through line 13 and is then condensed and separated into the different methylchlorosilane products. Periodically the powder deposited on the outside of filter elements 14 is blown back or removed by blowing gas through filter elements in a direction opposite to the flow direction of the chlorosilanes. Line 15 may be utilized for the purpose of the blowback process. The blowback can be methylchloride gas, inert gas or any other gas including the gaseous chlorosilanes. The blown powder leaves the vessel 12 through line 16 by gravity and is collected in hopper 17, the powder can then be transferred from hopper 17 through line 18 and is discarded or recycled in the same or some other process.

Thus, it can be seen that the process of the present invention makes it possible by a simple means to quantitatively separate essentially all of the silicon and copper residual powder contained in gaseous chlorosilanes before the reaction gas is condensed and without wasting valuable gaseous chlorosilane products nor expending costly energy for incinerating a slurry product. As a result of this process it is additionally possible to achieve a marked increase in silicon yield, i.e. the extent to which silicon can be utilized in making such chlorosilane products in the direct process. Furthermore, the reduction in waste and significant savings in energy are readily apparent from the above description.

The sintered metal filters used in the process of the present invention are commercially available products which can be obtained from several sources including Pall Trinity Micro Corporation of Cortland, N.Y., and Mott Metalurgical Corporation of Farmington, Conn.

These filters are generally produced by starting with stainless steel, nickel, Inconel or Monel metal powders. Useful grades of stainless steel include stainless steel 316, 304, and 347. These metal powders are laid in the form of a sheet and heated in a furnace in a reducing atmosphere. The temperature is raised to just below the melting point whereupon the particles fuse at points of contact thereby forming a sheet. The porous sheet is then rolled into a cylinder of desired diameter and welded at the seams, although seamless tubes are available. One end of the filter element is capped and the other end is fixed to the tube sheet support member within the filter vessel.

New filter elements have a characteristic pressure drop. When the filter becomes coated with powder the pressure drop becomes greater but upon blowback it returns to nearly the initial state. Initially for the first few cycles there will be some powder penetration of the filter element which will not be corrected by blowback, but after this point there will usually be no further powder penetration and a steady state operation for thousands of cycles can be expected.

Figure 2:
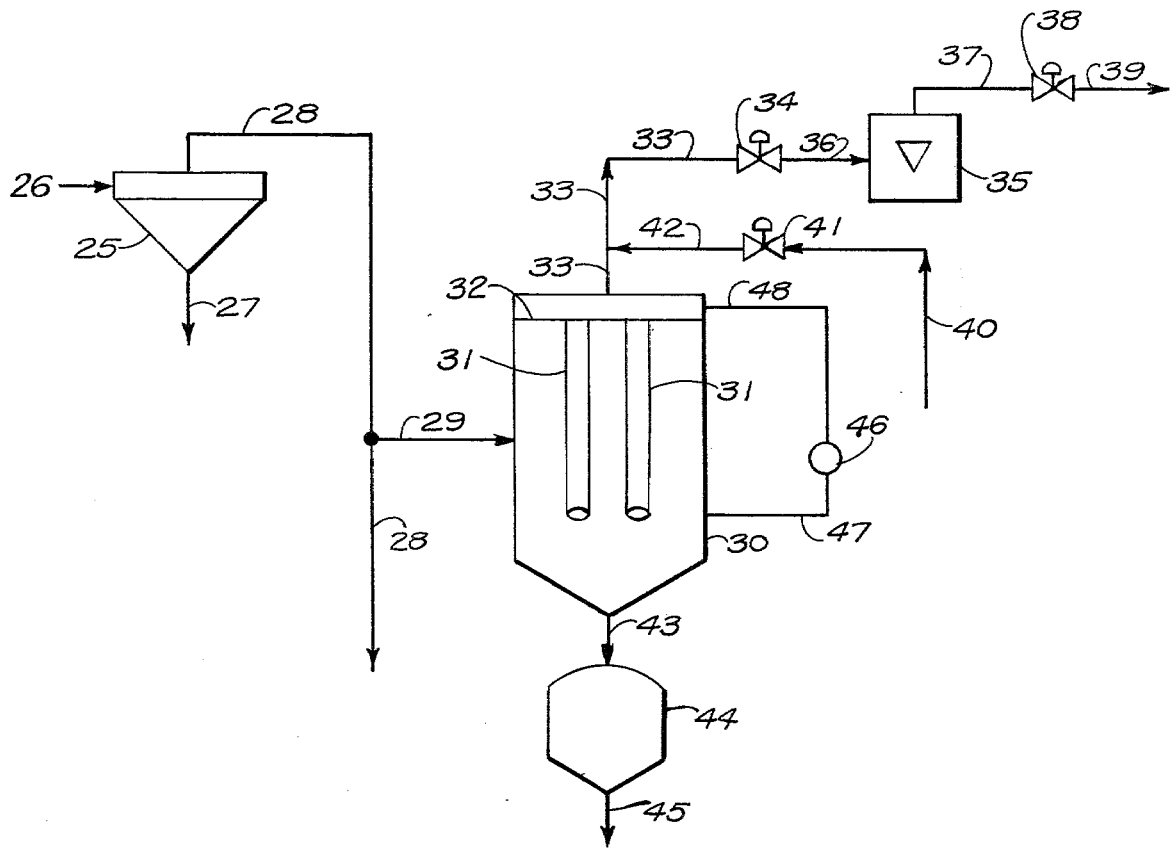
FIG. 2 is a process flow diagram depicting the organohalosilane gaseous crude purification process of the present invention utilizing a relatively more elaborate sintered metal filter array and blowback system.

A pilot unit utilizing the process of the present invention was constructed as shown schematically in FIG. 2. The unit was constructed with a side stream from a commercial methylchlorosilane process. Powder-laden crude gas from such a commercial reactor enters cyclone 25 through line 26. Most of the powder is separated from the gas stream in cyclone 25 and this powder leaves the cyclone through line 27. The remaining powder is then carried out of the cyclone by the gaseous chlorosilane reaction product through line 28. In this commercial process, the powder-laden gaseous crude then enters the scrubber which is not shown in FIG. 2 but has been described earlier, through line 28. A small stream of this powder-laden gaseous crude was directed into filter vessel 30 through line 29. The dust was deposited on the outside of two filter elements 31. The filter elements were supplied by Pall Trinity Micro Corporation. One element was made up of stainless steel 316 while the other element was made up of Inconel 600. The filter elements were suspended in vessel 30 by using a support member 32 called a tube sheet. The elements were 70 inches long and 2⅜ inches in diameter. Dust-free chlorosilanes passing through the filter elements leave the filter vessel through line 33 where they flow through valve 34 and enter flow meter 35 after passing through line 36. The flow meter 35 indicates the flow rate of chlorosilanes through the filter assembly. The flow rate is regulated at the desired level by adjustment of valve 38. The chlorosilanes leave the flow meter 35 through line 37, thereby flowing through valve 38 and line 39 and thereafter they may be condensed. Periodically the powder is blown off from the filter surface by blowing methylchloride vapors through line 40 and valve 4 and line 42 into the filter vessel 30 through line 33 and closing valve 34. The methylchloride vapors thus flow in the reverse direction and flow through the filter elements 31 into the vessel 30 when valve 34 is closed. This flow may last from one-half second to five seconds in the form of a pulse. The pulsing flow blows the dust from the outside of the filter surface. The dust passes through line 43 and into the vessel 44. From vessel 44 it may be collected through line 45. During the time when chlorosilanes were filtered, valve 34 is open and valve 41 is closed so as to prevent the flow of methylchloride. During blowback, valve 34 is closed and valve 41 is open. The operation of valves 34 and 41 is controlled in such a manner that when one closes the other one opens. The blowback operation may be carried out every few minutes depending on dust loading of the crude gaseous chlorosilanes. Pressure drop across the filter elements due to the dust buildup was measured by a differential pressure cell 46 connected to the high pressure side by line 47 and the low pressure side of the filter elements by the line 48. This differential pressure measurement can be an important evaluation for the performance of the filter elements.

In a test of the process of the present invention, the temperature of incoming dust-laden chlorosilane was 230° C. and the flow rate was such that the velocity across filter elements 31 was approximately 3 to 3.6 feet per minute. The pressure drop across the filter element due to dust buildup was approximately 0.5 to 0.6 psi before blowing back. The dust was blown back every 2 minutes and the length of blowback period was 2 seconds. After approximately 20 blowback cycles the pressure drop across the filter elements reached a steady value and remained so through the conclusion of the test. During the test, the total number of blowbacks were 116. A sample of collected powder was analyzed for silicon and copper content. The silicon content was 35% and copper content was 14% by weight. This powder was reacted with hydrochloridic acid gas in the laboratory. Approximately 46% of the available silicon was converted into useful chlorosilanes. About 85% of the chlorosilanes consisted of trichlorosilane and silicontetrachloride. Thus it is evident that the recovered residual powder may be readily converted into useful and valuable chlorosilane products.

What is claimed as new and desired to be protected by Letters Patent of the United States is:

1. A process for purifying gaseous organohalosilane products of a direct process reactor comprising the steps of:
   (a) directing a stream of powder-laden gaseous organohalosilane to a filter vessel containing filter array comprised of at least one sintered metal filter;
   (b) separating said powder from said gaseous organohalosilane by passing said gaseous organohalosilane through said sintered metal filter and depositing said powder upon an outer surface of said sintered metal filter;
   (c) recovering said powder from the surface of said filters by halting the flow of said gaseous organohalosilane and directing a stream of blowback gas through said filter in a direction opposite to said flow of gaseous organohalosilane; and
   (d) removing said powder from said filter vessel.

2. A process as in claim 1 which said organohalosilane products are methylchlorosilane products.

3. A process as in claim 1 wherein power-laden gaseous organohalosilane contains residual silicon and copper powders from said direct process reactor.

4. A process as in claim 1 wherein said blowback gas is selected from gaseous alkylchlorides and chlorosilanes.

5. A process as in claim 1 wherein said powder-laden organohalosilane is passed through said sintered metal filters under a pressure of 50 to 130 psi.

6. A process as in claim 1 wherein said blowback gas is periodically pulsed in said opposite direction for an amount of time effective for removing essentially all residual powder from said filters.

7. A process as in claim 6 wherein said pulse is approximately 0.5 to 5 seconds.

8. A process as in claim 6 wherein said periodic pulse is repeated such that the average pressure drop across said filters remains relatively constant.

9. A process as in claim 8 wherein said average pressure drop is approximately 0.2 to 3 psi.

10. A process as in claim 1 further comprising the step of recovering essentially powder-free organohalosilane products from said filter vessel.

11. A process as in claim 1 further comprising the step of recycling said powder and said blowback gas to said direct process reactor.

* * * * *